US009278298B2

(12) United States Patent
Takewaki et al.

(10) Patent No.: US 9,278,298 B2
(45) Date of Patent: Mar. 8, 2016

(54) OIL COMPOUND AND DEFOAMER COMPOSITION

(75) Inventors: Kazuyuki Takewaki, Annaka (JP); Chinami Matsui, Annaka (JP); Takato Sakurai, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 999 days.

(21) Appl. No.: 13/433,346

(22) Filed: Mar. 29, 2012

(65) Prior Publication Data

US 2012/0256624 A1    Oct. 11, 2012

(30) Foreign Application Priority Data

Apr. 7, 2011  (JP) .................................. 2011-085087

(51) Int. Cl.
| | |
|---|---|
| C09K 3/00 | (2006.01) |
| B01D 19/04 | (2006.01) |
| C11D 9/36 | (2006.01) |
| G01N 24/08 | (2006.01) |

(52) U.S. Cl.
CPC .............. *B01D 19/0409* (2013.01); *C11D 9/36* (2013.01); *G01N 24/087* (2013.01)

(58) Field of Classification Search
CPC ....................................................... C11D 9/225
USPC .......................................... 510/347, 122, 276
See application file for complete search history.

(56) References Cited

U.S. PATENT DOCUMENTS

| | | | |
|---|---|---|---|
| 3,865,544 A | 2/1975 | Keil | |
| 3,984,200 A | 10/1976 | Doesburg | |
| 3,984,347 A | 10/1976 | Keil | |
| 4,690,713 A | 9/1987 | Terae et al. | |
| 8,084,566 B2* | 12/2011 | Rautschek et al. | 528/29 |

(Continued)

FOREIGN PATENT DOCUMENTS

| | | |
|---|---|---|
| GB | 1204383 | 9/1970 |
| GB | 1468896 | 3/1977 |

(Continued)

OTHER PUBLICATIONS

Aramata et al., "Application of solid state 29Si NMR to an investigation of the silica-siloxane interface in a silicone elastomer," Bunseki Kagaku, vol. 47, No. 12, 1998, 9 pages (pp. 971-978).

(Continued)

*Primary Examiner* — Louis Arana
(74) *Attorney, Agent, or Firm* — Birch, Stewart, Kolasch & Birch, LLP (57) ABSTRACT

An oil compound used for defoaming includes (A) a substantially hydrophobic organopolysiloxane having a viscosity of 10 to 100,000 mm$^2$/second at 25° C., and (B) finely divided silica that has undergone surface hydrophobization treatment, wherein when an insoluble matter is collected from the oil compound by using hexane and the spectra of the insoluble matter are measured by $^{29}$Si-CP/MAS-NMR, the peaks of the silica due to the SiO$_{4/2}$ (Q) units on the silica surface are such that a ratio [(Q2+Q3)/Q4] between a total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group is at 70/30 to 20/80.

9 Claims, 3 Drawing Sheets

(56) References Cited

U.S. PATENT DOCUMENTS

| | | | |
|---|---|---|---|
| 8,536,109 B2 * | 9/2013 | Delbrassinne et al. | 510/347 |
| 2015/0119509 A1 * | 4/2015 | Brehm et al. | 524/147 |
| 2015/0165345 A1 * | 6/2015 | Merget et al. | 510/347 |

FOREIGN PATENT DOCUMENTS

| | | |
|---|---|---|
| JP | 51-71886 | 6/1976 |
| JP | 51-35556 | 10/1976 |
| JP | 52-19836 | 5/1977 |
| JP | 52-22638 | 6/1977 |
| JP | 52-31836 | 8/1977 |
| JP | 54-43015 B2 | 12/1979 |
| JP | 55-23084 B2 | 6/1980 |
| JP | 63-40717 A | 2/1988 |
| JP | 8-206409 A | 8/1996 |
| JP | 10-282027 A | 10/1998 |
| JP | 11-281598 A | 10/1999 |
| JP | 2005-324140 A | 11/2005 |
| JP | 2007-222812 A | 9/2007 |
| JP | 4232031 B2 | 3/2009 |

OTHER PUBLICATIONS

Japanese Office Action dated Sep. 24, 2014 for Japanese Application No. 2012-072948.

* cited by examiner

OIL COMPOUND AND DEFOAMER COMPOSITION

CROSS-REFERENCE TO RELATED APPLICATION

This non-provisional application claims priority under 35 U.S.C. §119(a) on Patent Application No. 2011-085087 filed in Japan on Apr. 7, 2011, the entire contents of which are hereby incorporated by reference.

TECHNICAL FIELD

This invention relates to an oil compound used for defoaming containing silica wherein the degree of hydrophobization of silanol groups on silica surface is controlled within a given range and more particularly, to an oil compound that is excellent in initial defoaming property and defoaming durability in foaming liquids, particularly alkaline foaming liquids, and also to a defoamer composition including the same.

BACKGROUND ART

Silicone defoamers have been widely used in the steps associated with foaming such as in the fields of chemical industries, food industries, petroleum industries, paper-making industries, textile industries, and pharmaceutical industries. There have been versatilely employed oil compound-type defoamers wherein silicone oils such as dimethylpolysiloxane, methylphenylpolysiloxane, and methylvinylpolysiloxane and the like and finely divided silica are mixed together.

In practical applications, there have been proposed emulsion defoamers wherein such oil compounds are dispersed in water along with surfactants, and self-emulsifying defoamers using polyoxyalkylene group-modified organopolysiloxanes and oil compounds in combination JP-A S51-71886, JP-B S54-43015, JP-B S52-19836, JP-B S52-22638 and JP-B S55-23084. The defoaming performance of these defoamers owes much to the starting oil compound, and related-art counterparts have been short of the defoaming performance in some cases. For one instance, some problems have arisen including the shortage of initial defoaming performance, the lowering of defoaming performance with time ascribed to long-term contact with foaming liquids, which have become pronounced, especially with the case where a foaming liquid is alkaline in nature.

A variety of proposals have been made in order to overcome these problems and more improve the defoaming performance. For instance, mention is made of a method wherein silica used in an oil compound has been preliminarily hydrophobized such as with chlorosilane in JP-B S52-31836 and a method of treating silica with a nitrogen-containing organosilicon compound in JP-B S51-35556. Nevertheless, the resulting performance has never been satisfactory and particularly, the defoaming performance has lowered with time in some cases. Thus, there has been a demand of further improving the performance.

In order to cope with these problems, there have been recently proposed a self-emulsifying defoamer composition in Japanese Patent No. 4232031 and an emulsion defoamer composition in JP-A 2007-222812 wherein hydrophobic organopolysiloxanes and finely divided silica surface-treated with an organopolysiloxane are treated under mixing in the presence of an alkaline catalyst to enhance an alkali resistance.

These defoamer compositions have a high defoaming performance, and such an alkali resistance as to undergo less time degradation in alkaline foaming liquids can be obtained. Nevertheless, the defoaming performance may become short under such severe conditions that a foaming liquid used is very high in alkalinity, an amount of a surfactant contained in a foaming liquid is very large, and an agitation force in an employed step is very intense. Thus, a further improvement of the performance has been demanded. In addition, with known defoamer compositions, a quantitative evaluation method for confirming a defoaming performance has never been known. Hence, evaluation has to be made for confirming the performance under practically employed conditions or similar conditions thereof on a case-by-case basis.

SUMMARY OF THE INVENTION

The invention has been made under the above circumstances. An object of the present invention is to provide an oil compound used for defoaming that has a good initial defoaming property in foaming liquids, particularly alkaline defoaming liquids, is reduced in time degradation and has excellent defoaming performance. Another object of the invention is to provide a defoamer composition including the above oil compound and a method for quantitatively evaluating a defoaming performance.

In order to achieve the above objects, we have made intensive studies and, as a result, found that an oil compound including finely divided silica whose surface silanol groups have undergone hydrophobization and wherein in the spectra measured by $^{29}$Si-CP/MAS (Cross Polarization)/(Magic Angle Spinning)-NMR, the peaks of the silica due to the $SiO_{4/2}$ (Q) units on the silica surface are such that a ratio [(Q2+Q3)/Q4] between a total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group is at 70/30 to 20/80, and preferably a ratio between the peak area of the triorganosiloxy units (M) and the peak area of the diorganosiloxy units (D) on the silica surface is at 80/20 to 10/90 is good at the initial defoaming property, is reduced in lowering of the performance with time and is excellent in defoaming performance.

Accordingly, the invention provides an oil compound used for defoaming, a defoamer composition comprising the same, and a method for evaluating a defoaming performance as follows.

[1] An oil compound used for defoaming comprising:
 (A) 100 parts by weight of a substantially hydrophobic organopolysiloxane having a viscosity of 10 to 100,000 mm$^2$/second at 25° C.; and
 (B) 1 to 20 parts by weight of finely divided silica that has undergone surface hydrophobization treatment,
wherein when an insoluble matter is collected from the oil compound by using hexane and the spectra of the insoluble matter are measured by $^{29}$Si-CP/MAS-NMR, the peaks due to $SiO_{4/2}$ (Q) units on the silica surface are such that a ratio [(Q2+Q3)/Q4] between the total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group, is at 70/30 to 20/80.

[2] The oil compound as defined in [1], wherein in the spectra measured by the $^{29}$Si-CP/MAS-NMR, a ratio (M/D) between the peak areas of triorganosiloxy units (M) and diorganosiloxy units (D) on the finely divided silica surface is at 80/20 to 10/90.

[3] The oil compound as defined in [1] or [2], wherein the oil compound is obtained by mixing the ingredient (A) and the ingredient (B) in the presence of an alkaline catalyst.

[4] A defoamer composition comprising the oil compound defined in any one of claims [1] to [3].

[5] The defoamer composition as defined in [4], wherein the composition is made of a solution dispersing the oil compound in a solvent.

[6] The defoamer composition as defined in [4], wherein the composition is of a self-emulsifying type wherein the oil compound is used in combination with an organopolysiloxane modified with a polyoxyalkylene group.

[7] The defoamer composition as defined in [4], wherein the composition is of an emulsion type wherein the oil compound is emulsified.

[8] A method for evaluating a deforming performance, characterized in that when an oil compound containing finely divided silica having undergone hydrophobization treatment on the surface thereof is subjected to collection of an insoluble matter therefrom by using hexane and the spectra of the insoluble matter are measured by $^{29}$Si-CP/MAS-NMR, the oil compound whose spectral peaks due to the $SiO_{4/2}$ (Q) units on the surface of the finely divided silica in the resulting spectra are such that a ratio [(Q2+Q3)/Q4] between a total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group is at 70/30 to 20/80, is evaluated as showing a good defoaming performance.

[9] A method for evaluating a deforming performance, characterized in that when an oil compound containing finely divided silica having undergone hydrophobization treatment on the surface thereof is subjected to collection of an insoluble matter therefrom by using hexane and the spectra of the insoluble matter are measured by $^{29}$Si-CP/MAS-NMR, the oil compound whose spectral peaks due to the $SiO_{4/2}$ (O) units on the surface of the finely divided silica are such that a ratio [(Q2+Q3)/Q4] between a total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group is at 70/30 to 20/80 and which has a ratio (M/D) between the peak area of triorganosiloxy units (M) and the peak area of diorganosiloxy units (D) on the finely divided silica surface being at 80/20 to 10/90, is evaluated as showing a good defoaming performance.

Advantageous Effects of the Invention

According to the invention, there can be provided a silicone-based oil compound and a defoamer composition, which have good initial defoaming property even in an alkaline foaming liquid, are inhibited from lowering the defoaming performance with time, and are excellent in defoaming performance. Additionally, there can also be provided a method for quantitatively evaluating the deforming performance.

DESCRIPTION OF THE EMBODIMENTS

The invention is now described in more detail.

Ingredient (A)

The organopolysiloxane used as ingredient (A) of the oil compound is substantially hydrophobic in nature. The term "substantially hydrophobic" used herein means that even if a hydrophilic group is contained as part of the functional groups, the organopolysiloxane shows hydrophobicity as a whole.

The substantially hydrophobic organopolysiloxane (A) may be linear or branched and is preferably one represented by the following average compositional formula (I):

$$R^1{}_m SiO_{(4-m)/2} \qquad (I)$$

In the above formula (I), $R^1$ is a substituted or unsubstituted monovalent hydrocarbon group having 1 to 18 carbon atoms and may be the same or different. Specific examples of the monovalent hydrocarbon group as $R^1$ include an alkyl group such as methyl group, ethyl group, propyl group, isopropyl group, butyl group, isobutyl group, pentyl group, hexyl group, heptyl group, octyl group, nonyl group, decyl group, dodecyl group, tridecyl group, tetradecyl group, hexadecyl group, or octadecyl group, a cycloalkyl group such as cyclohexyl group, an alkenyl group such as vinyl group or allyl group, an aryl group such as phenyl group or tolyl group, an aralkyl group such as styryl group or α-methylstyryl group, or those mentioned above wherein at least one of the hydrogen atoms bonded to the carbon atoms thereof are substituted with a halogen atom, a cyano group, an amino group, or a hydroxyl group, e.g., chloromethyl group, 3-chloropropyl group, 3,3,3-trifluoropropyl group, cyanoethyl group, 3-aminopropyl group, or N-(β-aminoethyl)-γ-amino propyl group. It is preferred from the standpoints of defoaming properties and economy that at least 80 mole %, more preferably at least 90 mole % of $R^1$ is methyl group. Letter m is a positive number of $1.9 \leq m \leq 2.2$, preferably $1.95 \leq m \leq 2.15$. It will be noted that the terminal ends of the organopolysiloxane may be blocked with either a triorganosilyl group represented by $R^1{}_3 Si$— or a diorganohydroxysilyl group represented by $(HO)R^1{}_2 Si$—.

From the standpoints of defoaming properties and workability, the viscosity of this substantially hydrophobic organopolysiloxane (A), measured at 25° C. by means of the Ostwald viscometer, is at 10 to 100,000 mm²/second, preferably at 50 to 30,000 mm²/second. If the viscosity is less than 10 mm²/second, the deforming performance degrades. If the viscosity is over 100,000 mm²/second, workability becomes worsened because of an increased viscosity of the resulting silicone oil compound.

Ingredient (B)

The finely divided silica used as ingredient (B) of the oil compound may be any of known ones including, for example, aerosol silica, precipitated silica, and pyrogenic silica. They may be used singly or in combination. The specific surface area of the finely divided silica (BET method) is preferably at least 50 m$^2$/g, more preferably 100 to 700 m$^2$/g, and much more preferably 150 to 500 m$^2$/g. If the specific surface area is less than 50 m$^2$/g, there may not be obtained a favorable deforming performance in some cases.

In the present invention, finely divided silica whose surface has been hydrophobized is used from the standpoint of defoaming property.

The amount of the finely divided silica is at 1 to 20 parts by weight, preferably at 5 to 15 parts by weight per 100 parts by weight of the organopolysiloxane (A). If the amount is less than 1 part by weight, the defoaming performance degrades and the amount exceeding 20 parts by weight leads to poor workability because of the increase in viscosity of the silicone oil compound.

The surface treated state of the finely divided silica and its measuring method are illustrated hereinbelow. For the solid NMR measurement of silicon, mention is made of a $^{29}$Si-DD/MAS (Dipolar Decoupled/Magnetic Angle Spinning)-NMR method and a $^{29}$Si-CP/MAS-NMR method. Of these, the $^{29}$Si-DD/MAS-NMR method is characterized in that all silicon atoms can be measured. On the other hand, the $^{29}$Si-CP/MAS-NMR method has such a feature that the nuclei of hydrogen atoms are excited and are subject to magnetization transfer to the nuclei of the neighboring silicon atoms, and only the nuclei of the silicon atoms undergoing the magnetization transfer are detected. If the time required for the magnetization transfer (contact time) is set at about 5 milliseconds, the silicon being detected is definitely limited in such a way that silicon atoms not present in the vicinity of hydrogen atoms and highly mobile silicon atoms such as in an oily form are unlikely to be detected.

Accordingly, when finely divided silica is measured according to the $^{29}$Si-CP/MAS-NMR method, silicon atoms inside the silica are not detected since no hydrogen atom is present in the vicinity thereof, but silicon atoms on the surface of silica can be detected because hydrogen atoms are present in the vicinity thereof in the form of a silanol group or a surface-treated group fixed to the silanol group. This is used to permit the silicon atoms alone on the silica surface to be selectively measured, thereby enabling the surface state of the finely divided silica to be quantitatively evaluated.

In the $^{29}$Si-CP/MAS-NMR, the surface treated group fixed to the finely divided silica is also selectively detected.

It will be noted that a surface treating agent or an oily ingredient, which does not react with a silanol group and is not fixed to the silica surface, cannot adequately undergo magnetization transfer from the nucleus of hydrogen atom, so that its sensitivity is low when measured by the $^{29}$Si-CP/MAS-NMR method, with little detection.

The spectra measured according to the $^{29}$Si-CP/MAS-NMR method can be generally attributed to the following ones relative to TMS (tetramethylsilane) as a reference.

25 to −10 ppm: R$^2$R$^3$R$^4$SiO$_{1/2}$ [triorganosiloxy unit: hereinafter abbreviated as M] (wherein R$^2$, R$^3$, —H, —C$_2$H$_5$, —CH=CH$_2$, or —C$_6$H$_5$)

−10 to −50 ppm: R$^2$R$^3$SiO$_{2/2}$ [diorganosiloxy unit: hereinafter abbreviated as D] (wherein R$^2$, R$^3$: —H, —C$_2$H$_5$, —CH=CH$_2$, or —C$_6$H$_5$)

−50 to −85 ppm: R$^2$SiO$_{3/2}$ [monoorganosiloxy unit: hereinafter abbreviated as T] (wherein R$^2$: —H, —CH$_3$, —C$_2$H$_5$, —CH=CH$_2$, or —C$_6$H$_5$)

−85 to −120 ppm: SiO$_{4/2}$ [hereinafter abbreviated as Q]

As to the SiO$_{4/2}$ unit among the above units, a peak Q2 of a silicon atom having two unreacted silanol groups, a peak Q3 of a silicon atom having one unreacted silanol group, and a peak Q4 of a silicon atom having no unreacted silanol group are, respectively, observed, with the attributions relative to TMS reference being generally as shown below.

−85 to −95 ppm: Q2
−95 to −105 ppm: Q3
−105 to −120 ppm: Q4

In the above, Q4 corresponds to one wherein all the silanol groups are reacted with a surface treating agent, and the surface treating agent for silica is generally a hydrophobizing agent, so that larger content of Q4 results in a higher degree of hydrophobization of silica as a whole.

More particularly, when the peak areas of silanol groups are measured by $^{29}$Si-CP/MAS-NMR, the degree of hydrophobization of finely divided silica can be expressed by a ratio [(Q2+Q3)/Q4] between the total peak areas (Q2+Q3) of the unreacted silanol groups on the silica surface and the peak area (Q4) of the silanol group on the silica surface that has no unreacted silanol group as a result of reaction with a surface hydrophobizing agent. A higher value of the ratio leads to a lower degree of hydrophobization, or a smaller value results in a higher degree of hydrophobization.

A good defoaming performance can be obtained when using finely divided silica whose value of (Q2+Q3)/Q4 is at 70/30 to 20/80, preferably at 65/35 to 30/70 and more preferably at 60/40 to 40/60. If the value is greater than 70/30, the degree of hydrophobization of such finely divided silica becomes low and thus, the silica is high in hydrophilicity, so that a satisfactory deforming performance cannot be obtained. Especially, defoaming durability in an alkaline foaming liquid becomes poor. To obtain silica having a value of smaller than 20/80 is difficult to prepare.

A good defoaming performance is ensured when using finely divided silica, which has a ratio (M/D) between the peak area of triorganosiloxy units (M) and the peak area of diorganosiloxy units (D), as measured by the $^{29}$Si-CP/MAS-NMR, of 80/20 to 10/90, preferably 70/30 to 20/80 and more preferably 60/40 to 30/70. If the value is greater than 80/20 or is smaller than 10/90, good defoaming properties cannot be obtained and especially, a defoaming performance immediately after addition an alkaline foaming liquid, i.e. an initial defoaming property, may become poor.

Finely divided silica whose surface has been hydrophobized is used as finely divided silica of the invention. The hydrophobization treatment on the surface of finely divided silica can be carried out by the known procedures. More particularly, the hydrophobization treatment can be carried out by treating hydrophilic silica with an organosilicon compound (surface hydrophobizing agent) such as an organochlorosilane, an organoalkoxysilane, an organodisilazane, an organopolysiloxane, or an organohydrogensilane. In this case, although there may be used finely divided silica that has been preliminarily surface-treated, it is preferred in the present invention to mix such preliminarily surface-treated, finely divided silica or finely divided silica not subjected to surface hydrophobizing treatment with the ingredient (A), thereby further surface-treating the finely divided silica to set (Q2+Q3)/Q4 and M/D at such values as defined before.

In this case, in order to set. (Q2+Q3)/Q4 and M/D at such values as defined above, it is effective for the preparation of an oil compound by mixing the ingredients (A) and (B) to add the surface hydrophobizing agent as described above, if necessary, and carry out the mixing at a temperature of room temperature (25° C.) to 200° C., preferably 100 to 200° C. and more preferably 120 to 180° C. If necessary, there may be added the organosilicon compound used for silica surface treatment as described above and an alkaline catalyst used to carry out reliable hydrophobization treatment by reaction for adsorption of the ingredient (A) on the surface of the ingredient (B), thereby permitting the treatment of the finely divided silica simultaneously. Under conditions of adding an alkaline catalyst, a neutralizing agent may be added, if necessary, after the mixing treatment so as to carry out the neutralization reaction and remove the resulting neutral salt by a filtration step. If necessary, an unreacted organosilicon compound and low boiling fractions may be removed.

It will be noted that the mixing time ranges 10 minutes to 5 hours, preferably 1 to 3 hours. The mixing is preferably carried out in an inert atmosphere such as of nitrogen.

The alkaline catalysts may be a known alkaline catalyst used for transfer reaction of polysiloxane, for which there can be used alkali metal or alkaline earth metal oxides, hydroxides, alkoxides or siliconates, of which potassium siliconate and potassium hydroxide are preferred.

The amount of the alkaline catalyst is in the range of 0.001 to 5 parts by weight, preferably from 0.01 to 3 parts by weight and more preferably from 0.05 to 2 parts by weight per 100 parts by weight of the organopolysiloxane (A). If the amount is less than 0.001 part by weight, there may be some cases where the effect as a catalyst is weak. The amount over 5 parts by weight may not be significantly improved with respect to the catalytic effect, thus leading to economic disadvantage.

Kneaders used for kneading in the method of the invention include, for example, gate mixers, kneaders, press kneaders, biaxial kneaders, and intensive mixers although not limited thereto. These kneaders can be used in any of steps including the mixing of the ingredients (A) and (B), the surface treatment of silica and a subsequent neutralization step.

Defoamer Composition

The silicone oil compound obtained according to the above steps may be used as it is, or may be used as a defoaming composition containing the silicone oil compound. Specifically, such a composition includes a solution-type defoaming composition dispersing it in an appropriate solvent, a self-emulsifying defoaming composition using in combination with an organopolysiloxane modified with a polyoxyalkylene group, or an emulsion-type defoaming composition obtained by known emulsification techniques.

Where a solution-type defoaming composition dispersing the silicone oil compound in an appropriate solvent is prepared, a solvent capable of dissolving the substantially hydrophobic organopolysiloxane used as the ingredient (A) is used including, for example, toluene, xylene, hexane, chloroform, 2-butanone, and 4-methyl-2-pentanone.

When prepared as the solution-type defoaming composition, the content of the silicone oil compound is preferably at 5 to 80% by weight, more preferably at 30 to 70% by weight, of the whole defoaming composition. If a lower content of the silicone oil compound may lead to a poor defoaming performance when used as a defoaming composition, and a larger content may not satisfy the primary purpose of the solution-type defoaming composition that dispersibility of an oil compound ingredient is enhanced.

In the case where a self-emulsifying defoaming composition using, in combination, an organopolysiloxane modified with a polyoxyalkylene group is prepared, the organopolysiloxane modified with a polyoxyalkylene group includes one represented by the following general formula (II):

$$R^5_2R^7SiO-(R^5_2SiO)_x-(R^5R^6SiO)_y-SiR^5_2R^7 \quad (II)$$

In the formula (II), $R^5$ may be the same or different and represents a substituted or unsubstituted monovalent hydrocarbon group having 1 to 18 carbon atoms. Specific examples include an alkyl group such as methyl group, ethyl group, propyl group, isopropyl group, butyl group, isobutyl group, pentyl group, hexyl group, heptyl group, octyl group, nonyl group, decyl group, dodecyl group, tridecyl group, tetradecyl group, hexadecyl group, or octadecyl group, a cycloalkyl group such as cyclohexyl group, an alkenyl group such as vinyl group or allyl group, an aryl group such as phenyl group or tolyl group, an aralkyl group such as styryl group or α-methylstyryl group, and those groups indicated above wherein at least one of the hydrogen atoms bonded to the carbon atoms thereof are substituted with a halogen atom, a cyano group, or an amino group, e.g., chloromethyl group, 3-chloropropyl group, 3,3,3-trifluoropropyl group, cyanoethyl group, 3-aminopropyl group, or N-(β-aminoethyl)-γ-aminopropyl group.

$R^6$ is a polyoxyalkylene group represented by the following general formula (III):

$$-R^8-O(CH_2CH_2O)_a-(CH_2(CH_3)CHO)_b-R^9 \quad (III)$$

In the above formula (III), $R^8$ represents a divalent hydrocarbon group having 2 to 6 carbon atoms including an alkylene group, or an alkenylene group. Mention is made, for example, of ethylene group, propylene group, butylene group, pentylene group, or hexylene group. $R^9$ represents hydrogen atom, an alkyl group having 1 to 6 carbon atoms, an acetyl group or an isocyan group. Examples of the alkyl group include methyl group, ethyl group, propyl group, butyl group, or pentyl group. Letters a and b are, respectively, such positive values that satisfy $3 \leq a+b \leq 80$, preferably $5 \leq a+b \leq 60$, and $a/b=2/8$ to $8/2$, preferably $a/b=2.5/7.5$ to $7.5/2.5$.

$R^7$ is a group similar to that of $R^5$ or $R^6$, hydroxyl group or an alkoxy group having 1 to 6 carbon atoms. Specific examples include those groups exemplified as $R^5$ and $R^6$, and examples of an alkoxy group include methoxy group, ethoxy group, propoxy group, or butoxy group.

In the formula (II), x is an integer of 5 to 200, preferably 20 to 150, and y is an integer of 1 to 30, preferably 1 to 20.

This polyoxyalkylene-modified organopolysiloxanes may be used singly or in admixture thereof, and there can be used those having a viscosity, measured at 25° C. by the Ostwald viscometer, of 10 to 10,000 mm²/second, preferably 50 to 8,000 mm²/second and much more preferably 500 to 5,000 mm²/second.

Specific examples of the polyoxyalkylene-modified organopolysiloxane include those indicated below although not limited thereto.

$$(CH_3)_3SiO-[(CH_3)_2SiO]_{30}-[(CH_3)R'SiO]_5-Si(CH_3)_3$$

wherein $R'=-C_3H_6O-(C_2H_4O)_{30}-(C_3H_6O)_{10}-C_4H_9$.

$$(CH_3)_3SiO-[(CH_3)_2SiO]_{30}-[(CH_3)R'SiO]_3-Si(CH_3)_3$$

wherein $R'=-C_3H_6O-(C_2H_4O)_{20}-(CH_4H_9$.

$$(CH_3)_3SiO-[(CH_3)_2SiO]_{40}-[(CH_3)R'SiO]_4-Si(CH_3)_3$$

wherein $R'=-C_3H_6O-(C_2H_4O)_{21}-(C_3H_6O)_7-COCH_3$.

$$(CH_3)_3SiO-[(CH_3)_2SiO]_{50}-[(CH_3)R''SiO]_6-[(CH_3)R'''SiO]_1-Si(CH_3)_3$$

wherein $R''=-C_3H_6O-(C_2H_4O)_{32}-(C_3H_6O)_8-C_4H_9$ and $R'''=-C_{12}H_{25}$.

$$(CH_3)_3SiO-[(CH_3)_2SiO]_{135}-[(CH_3)R'SiO]_{15}-Si(CH_3)_3$$

wherein $R'=-C_3H_6O-(C_2H_4O)_{21}-(C_3H_6O)_{21}-CH_3$.

$$(CH_3)_3SiO-[(CH_3)_2SiO]_{30}-[(CH_3)R'SiO]_5-Si(CH_3)_3$$

wherein R'=—C₃H₆O—(C₂H₄O)₂₅.₅—(C₃H₆O)₈.₅—C₄H₉.

wherein R'=—C₃H₆O—(C₂H₄O)₂₃—(C₃H₆O)₂₃—C₄H₉.

For the self-emulsifying defoaming composition using in combination with the polyoxyalkylene-modified organopolysiloxane, there may be further used polyoxyalkylene polymers exemplified as and and nonionic surfactants such as sorbitan fatty acid esters, glycerine fatty acid esters, polyglycerine fatty acid esters, propylene glycol fatty acid esters, sucrose fatty acid esters, polyoxyethylene alkyl ethers, polyoxyethylene oxypropylene alkyl ethers, polyoxyethylene fatty acid esters, polyoxyethylene sorbitan fatty acid esters, polyoxyethylene glycerine fatty acid esters, polyoxyethylene propylene glycol fatty acid esters, polyoxyethylene castor oil, and polyoxyethylene hardened castor oil. It will be noted that the above-exemplified compositional formulas are indicated by way of example, and the invention should not be construed as limited thereto.

With the self-emulsifying defoaming composition, the content of the silicone oil compound is preferably at 5 to 80% by weight, more preferably at 10 to 70% by weight and much more preferably at 20 to 60% by weight of the whole defoaming composition. If the content of the silicone oil compound is smaller, there may be the case where the defoaming performance of the resulting defoaming composition becomes poor. A larger content may lead to the case where the primary purpose of the self-emulsifying defoaming composition that dispersibility of the oil compound ingredient is enhanced cannot be satisfied.

The content of the polyoxyalkylene polymer and/or the nonionic surfactant is preferably 0 to 90% by weight, more preferably 0 to 70% by weight of the whole defoaming composition. The content of the organopolysiloxane modified with a polyoxyalkylene group is the balance, although it is preferably contained in an amount of at least 20% by weight, more preferably at least 30% by weight, much more preferably at least 40% by weight of the whole defoaming composition.

Further, when prepared as an emulsion-type defoaming composition, known procedures can be used, and emulsifiers used to emulsify the silicone oil compound includes such polyoxyalkylene-modified organopolysiloxanes, polyoxyalkylene polymers, and nonionic surfactants as described above.

The polyoxyalkylene-modified organopolysiloxanes of the emulsion-type defoaming composition may be used singly or in admixture of at least two. The content is preferably at 0 to 30% by weight, more preferably at 1 to 20% by weight of the whole defoaming composition. When the content exceeds 30% by weight, there may be the case where the defoaming performance of the composition becomes poor.

In the emulsion-type defoaming composition, the polyoxyalkylene polymers serve as an emulsification aid and may be used singly or in admixture of at least two. The content is preferably at 0 to 40% by weight, more preferably at 0 to 20% by weight, of the whole defoaming composition. If the content exceeds 40% by weight, there may be the case where the emulsifying characteristics of the composition become poor. It will be noted that if formulated, the polymer is used in an effective amount and preferably, at least 5% by weight is formulated.

In the emulsion-type defoaming composition, the nonionic surfactants are used to disperse a silicone oil compound in water and may be used singly or in admixture of at least two. The content is preferably at 0 to 20% by weight, more preferably at 1 to 10% by weight, of the whole defoaming composition. If the content exceeds 20% by weight, the defoaming composition becomes high in viscosity, so that workability becomes poor.

The total amount of the emulsifier such as the polyoxyalkylene-modified organopolysiloxane, the polyoxyalkylene polymer and the nonionic surfactant is preferably 1 to 40% by weight, more preferably 5 to 20% by weight of the whole defoaming composition.

When the emulsion-type defoaming composition is prepared, the content of the silicone oil compound is preferably at 5 to 50% by weight, more preferably at 10 to 40% by weight, of the whole defoaming composition. If the content of the silicone oil compound is smaller, there may be the case that the defoaming performance as a defoaming composition becomes poor. If the content of the silicon oil compound is larger, the defoaming composition becomes high in viscosity, so that workability becomes worsened.

In the emulsion-type defoaming composition, it is necessary to add water required for emulsifying the respective ingredients including a silicone oil compound, a polyoxyalkylene-modified organopolysiloxane, a polyoxyalkylene polymer, and a nonionic surfactant. The amount is the balance relative to the total of the contents of the respective ingredients and is preferably at 50 to 2,000 parts by weight, more preferably at 80 to 400 parts by weight, per 100 parts of the total content of the respective ingredients.

It will be noted that the emulsion-type defoaming composition can be prepared by mixing given amounts of the respective ingredients except for water and emulsifying under agitation, while heating if necessary, by known methods using a mixer or dispersing machine such as, for example, a homo mixer, a homogenizer, or a colloid mill. Especially, it is preferred to uniformly mix and disperse given amounts of the respective ingredients except for water, adding part of water, followed by emulsification under agitation and uniform mixing under agitation after addition of the rest of water.

The emulsion-type defoaming composition may be optionally admixed with small amounts of preservatives and bactericides for the purpose of preservation. Specific examples of the preservative and bactericide include sodium hypochlorite, sorbic acid, potassium sorbate, salicylic acid, sodium salicylate, benzoic acid, sodium benzoate, parabens, and an isothiazoline compound. The amount is at 0 to 0.5% by weight, preferably at 0.005 to 0.5% by weight of the whole emulsion-type defoaming composition.

Further, the emulsion-type defoaming composition may be optionally admixed with a small amount of a thickener for the purpose of viscosity increase. Specific examples of the thickener include polyacrylic acid, sodium polyacrylate, acrylic acid/methacrylic acid copolymer, sodium carboxymethyl cellulose, methyl cellulose, hydroxypropyl methylcellulose, hydroxyethyl methylcellulose, xanthan gum, and guar gum. The amount is at 0 to 1.0% by weight, preferably at 0.01 to 0.5% by weight of the whole emulsion-type defoaming composition.

EXAMPLES

Examples and Comparative Examples are shown to particularly illustrate the invention although the invention should not be construed as limited to the following Examples. In the following Examples, viscosity is a value measured at 25° C. by means of an Ostwald viscometer.

Example 1

100 parts by weight of dimethylpolysiloxane, which was used as a substantially hydrophobic organopolysiloxane, had a viscosity of 10,000 mm$^2$/second and was blocked with a trimethylsilyl group at opposite terminal ends of the molecule chain, 5 parts by weight of Aerosil R812 (made by Nippon Aerosil Co., Ltd., and having a specific surface area of 260 m$^2$/g) used as finely divided silica and 1 part by weight of potassium siliconate containing 3% by weight of potassium hydroxide and used as a an alkaline catalyst were provided and kneaded in an atmosphere of nitrogen gas at 150° C. for 3 hours by use of a gate mixer. After cooling down up to 100° C., the mixture was neutralized with 2-chloroethanol, followed by removal of low boiling fractions to obtain silicone oil compound (a-1).

Figure 1:
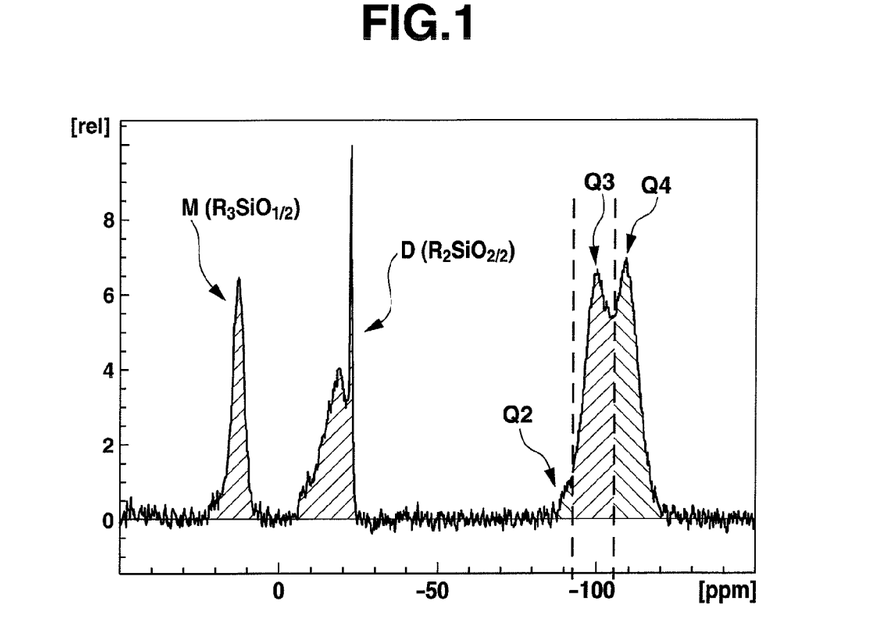
FIG. 1 is a chart showing $^{29}$Si-CP/MAS-NMR spectra of an insoluble matter in an oil compound obtained in Example 1.

Hexane was used to collect an insoluble matter from the oil compound (a-1) and the insoluble matter was subjected to measurement with $^{29}$Si-CP/MAS-NMR (Model AVANCE 700, made by BRUKER Inc., 700 MHz), revealing that (Q2+Q3)/Q4=47/53 and M/D=35/65. The resulting chart is shown in FIG. 1.

30 parts by weight of this silicone oil compound (a-1) and 70 parts by weight of a polyoxyalkylene-modified organosiloxane (a-2) of the average composition represented by the following formula $R^5{}_2R^7SiO\text{—}(R^5{}_2)_x\text{—}(R^5R^6SiO)_y\text{—}SiR^5{}_2R^7$ wherein $R^5$ and $R^7$ are, respectively, —CH$_3$, $R^6$ is —C$_3$H$_6$O(C$_3$H$_4$O)$_{21}$(C$_3$H$_6$O)$_{21}$CH$_3$, x is 135 and y is 15, and having a viscosity of 2,500 mm$^2$/second were mixed together at room temperature to prepare defoaming composition (A).

Example 2

A mixture of 20 parts by weight of the silicone oil compound (a-1) of Example 1, 4 parts by weight of sorbitan monostearate and 6 parts by weight of polyoxyethylene (55) monostearate was dissolved under heating, to which 70 parts by weight of water was added, followed by agitation and emulsification with a homo mixer to prepare defoaming composition (B).

Example 3

100 parts by weight of dimethylpolysiloxane, which was used as a substantially hydrophobic organopolysiloxane, had a viscosity of 8,000 mm$^2$/second and was blocked with a trimethylsilyl group at the terminal end of the branched molecular chain containing CH$_3$SiO$_{3/2}$ unit at a molar fraction of 0.01, 12 parts by weight of Nipsil HD-2 (made by Tosoh Silica Corporation and having a specific surface area of 300 m$^2$/g) used as finely divided silica, and 1.0 part by weight of hexamethyldisilazane used as a silica surface treating agent were added and kneaded in an atmosphere of nitrogen gas at 150° C. for 1 hour by use of a gate mixer. After cooling down up to 100° C., 1.8 parts by weight of hexamethyldisilazane was added, followed by kneading at 150° C. for 3 hours. After cooling, the resulting mixture was filtered through a nylon mesh to obtain silicone oil compound (c-1).

Figure 2:
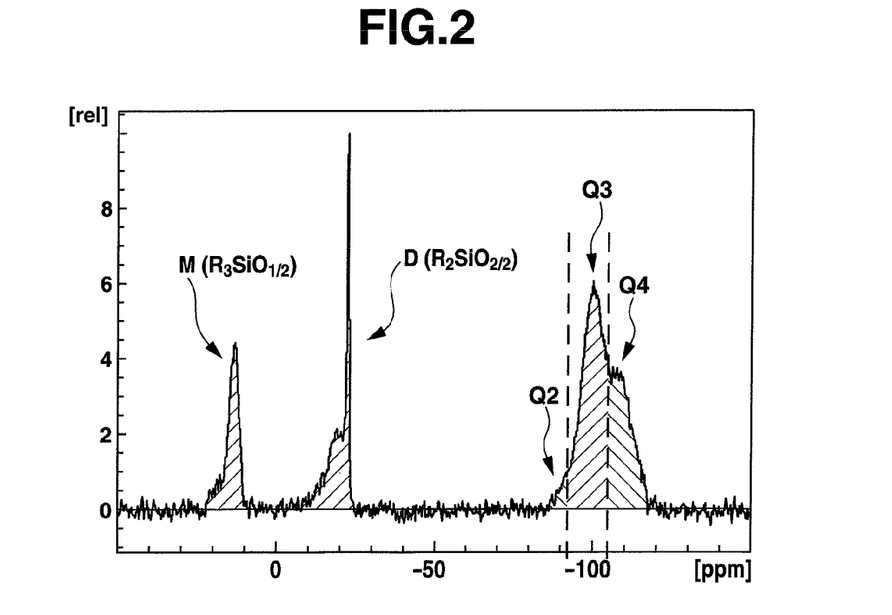
FIG. 2 is a chart showing $^{29}$Si-CP/MAS-NMR spectra of an insoluble matter in an oil compound obtained in Example 3.

Hexane was used to collect an insoluble matter from the oil compound (c-1), followed by measurement of the insoluble matter with $^{29}$Si-CP/MAS-NMR, revealing that (Q2+Q3)/Q4=63/47 and M/D=48/52. The resulting chart is shown in FIG. 2.

30 parts by weight of this silicone oil compound (c-1), 50 parts by weight of a polyoxyalkylene-modified organosiloxane (c-2) of the average composition represented by the following formula $R^5{}_2R^7SiO\text{—}(R^5{}_2SiO)_x\text{—}(R^5R^6SiO)_y\text{—}SiR^5{}_2R^7$ wherein $R^5$ and $R^7$ are, respectively, —CH$_3$, $R^6$ is —C$_3$H$_6$O(C$_2$H$_4$O)$_{25.5}$(C$_3$H$_6$O)$_{8.5}$C$_4$H$_9$, x is 30 and y is 5, and having a viscosity of 1,000 mm$^2$/second, and 20 parts by weight of a polyoxyalkylene polymer (c-3) whose average composition was represented by the following formula

HO—(C$_2$H$_4$O)$_{25}$—(C$_3$H$_6$O)$_{35}$—H were mixed together at room temperature to prepare defoaming composition (C).

Example 4

100 parts by weight of dimethylpolysiloxane, which was used as a substantially hydrophobic organopolysiloxane, had a viscosity of 10,000 mm$^2$/second and was blocked with a trimethylsilyl group at opposite terminal ends of the molecule chain, 8 parts by weight of Aerosil R202 (made by Nippon Aerosil Co., Ltd., and having a specific surface area of 100 m$^2$/g) used as finely divided silica and 0.005 parts by weight of potassium hydroxide used as a an alkaline catalyst were provided and kneaded in an atmosphere of nitrogen gas at 150° C. for 3 hours by use of a gate mixer. After cooling down up to 100° C., the mixture was neutralized with 0.003 parts by weight of succinic acid, followed by filtration with a nylon mesh to obtain silicone oil compound (d-1).

Figure 3:
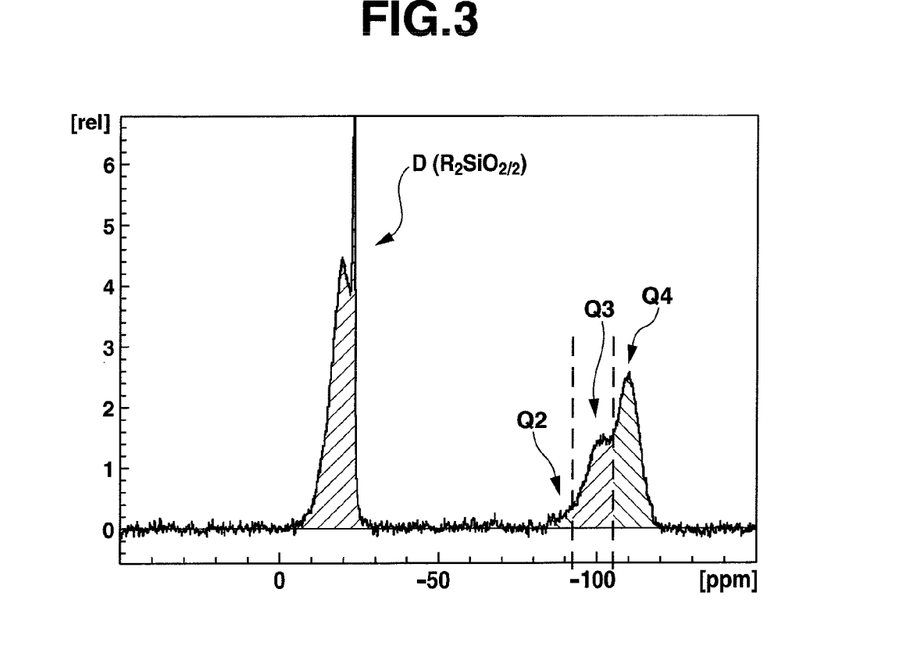
FIG. 3 is a chart showing $^{29}$Si-CP/MAS-NMR spectra of an insoluble matter in an oil compound obtained in Example 4.

Hexane was used to collect an insoluble matter from the oil compound (d-1), followed by measurement of the insoluble matter with $^{29}$Si-CP/MAS-NMR, revealing that (Q2+Q3)/Q4=42/58 and M/D=0/100. The resulting chart is shown in FIG. 3.

30 parts by weight of this silicone oil compound (d-1), 50 parts by weight of a polyoxyalkylene-modified organosiloxane (d-2) of the average composition represented by the following formula $R^5{}_2R^7SiO\text{—}(R^5{}_2SiO)_x\text{—}(R^5R^6SiO)_y\text{—}SiR^5{}_2R^7$ wherein $R^5$ and $R^7$ are, respectively, —CH$_3$, $R^6$ is —C$_3$H$_6$O(C$_2$H$_4$O)$_{23}$(C$_3$H$_6$O)$_{23}$C$_4$H$_9$, x is 27 and y is 3, and having a viscosity of 1,700 mm$^2$/second, and 20 parts by weight of a polyoxypropylene polymer (d-3) of the average composition represented by the following formula

HO—(C$_3$H$_6$O)$_{30}$—H were mixed together at room temperature to prepare defoaming composition (D).

Example 5

A mixture of 20 parts by weight of the silicone oil compound (d-1) of Example 4, 6 parts by weight of sorbitan monostearate, and 6 parts by weight of polyoxyethylene (55) monostearate was dissolved under heating, to which 68 parts by weight of water was added, followed by agitation and emulsification with a homo mixer to prepare defoaming composition (E).

Comparative Example 1

100 parts by weight of dimethylpolysiloxane, which was used as a substantially hydrophobic organopolysiloxane, had a viscosity of 10,000 mm²/second and was blocked with a trimethylsilyl group at opposite terminal ends of the molecule chain, and 5 parts by weight of Aerosil R812 (made by Nippon Aerosil Co., Ltd., and having a specific surface area of 260 m²/g) used as finely divided silica were provided and kneaded in an atmosphere of nitrogen gas at 150° C. for 3 hours by use of a gate mixer to obtain silicone oil compound (f-1).

Figure 4:
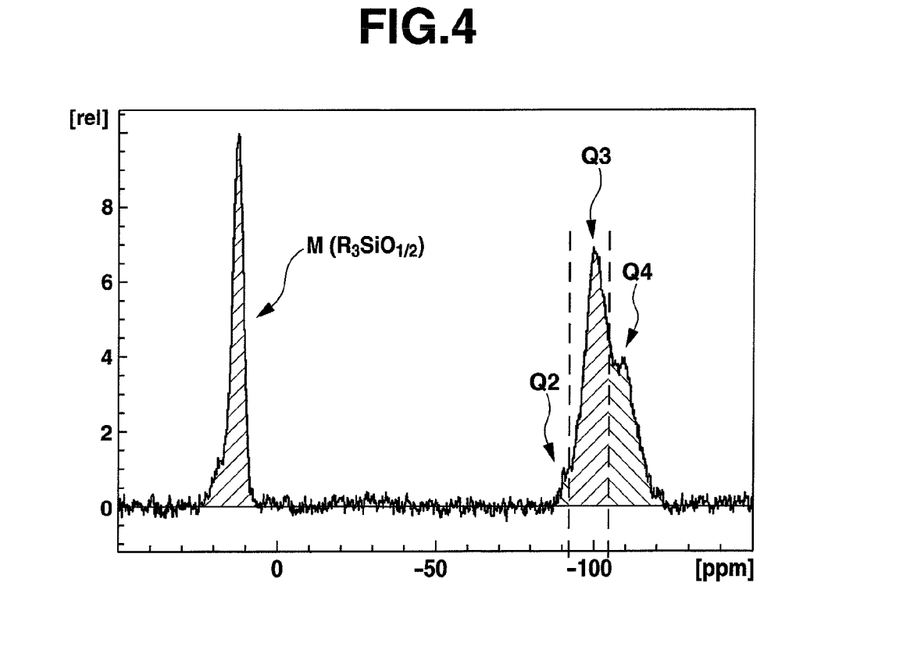
FIG. 4 is a chart showing $^{29}$Si-CP/MAS-NMR spectra of an insoluble matter in an oil compound obtained in Comparative Example 1.

Hexane was used to collect an insoluble matter from the oil compound (f-1), followed by measurement of the insoluble matter with ²⁹Si-CP/MAS-NMR, revealing that (Q2+Q3)/Q4=72/28 and M/D=100/0. The resulting chart is shown in FIG. 4.

30 parts by weight of this silicone oil compound (f-1) and 70 parts by weight of a polyoxyalkylene-modified organosiloxane (f-2) of the average composition represented by the following formula wherein $R^5$ and $R^7$ are, respectively, —CH₃, $R^6$ is —C₃H₆O(C₂H₄O)₂₁(C₃H₆O)₂₁CH₃, x is 135 and y is 15, and having a viscosity of 2,500 mm²/second, were mixed together at room temperature to prepare defoaming composition (F).

Comparative Example 2

A mixture of 20 parts by weight of the silicone oil compound (f-1) in Comparative Example 1, 4 parts by weight of sorbitan monostearate and 6 parts by weight of polyoxyethylene (55) monostearate was dissolved under heating, to which 68 parts by weight of water was added, followed by agitation and emulsification with a homo mixer to prepare defoaming composition (G).

Comparative Example 3

100 parts by weight of dimethylpolysiloxane, which was used as a substantially hydrophobic organopolysiloxane, had a viscosity of 8,000 mm²/second and was blocked with a trimethylsilyl group at the terminal ends of the branched molecule chain containing SiO₃/₂ unit at a molar fraction of 0.01, and 12 parts by weight of Nipsil HD-2 (made by Tosoh Silica Corporation and having a specific surface area of 300 m²/g) used as finely divided silica were provided and kneaded in an atmosphere of nitrogen gas at 150° C. for 3 hours by use of a gate mixer to obtain silicone oil compound (h-1).

Figure 5:
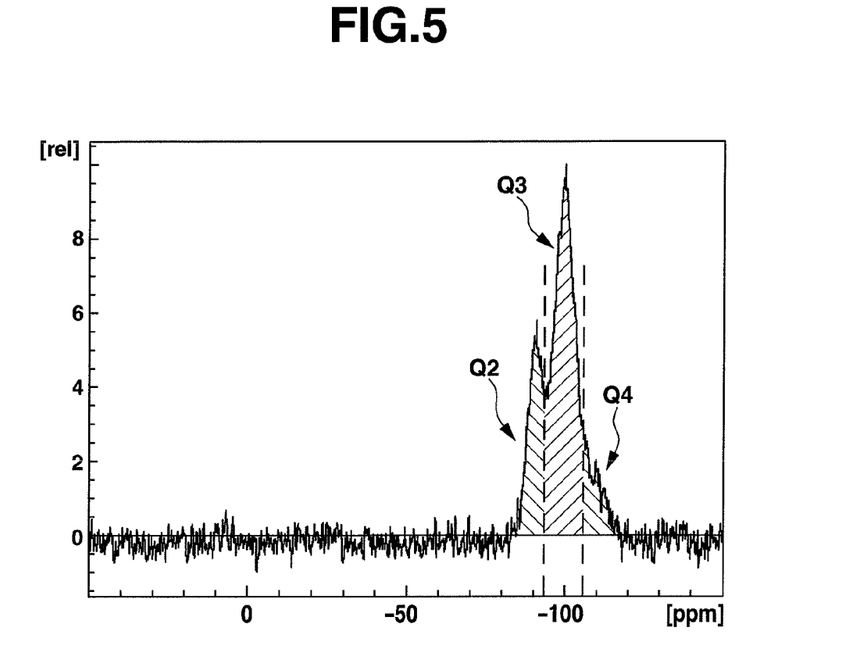
FIG. 5 is a chart showing $^{29}$Si-CP/MAS-NMR spectra of an insoluble matter in an oil compound obtained in Comparative Example 1.

Hexane was used to collect an insoluble matter from the oil compound (h-1), followed by measurement of the insoluble matter with ²⁹Si-CP/MAS-NMR, revealing that (Q2+Q3)/Q4=88/12 and M/D was such that since no silica surface treatment was carried out, both were zero. The resulting chart is shown in FIG. 5.

30 parts by weight of this silicone oil compound (h-1) and 70 parts by weight of a polyoxyalkylene-modified organosiloxane (h-2) of the average composition represented by the following formula wherein $R^5$ and $R^7$ are, respectively, —CH₃, $R^6$ is —C₃H₆O(C₃H₄O)₂₁(C₃H₆O)₂₁CH₃, x is 135 and y is 15, and having a viscosity of 2,500 mm²/second, were mixed together at room temperature to prepare defoaming composition (H).

The defoaming compositions obtained in Examples 1 to 5 and Comparative Examples 1 to 3 were evaluated according to the following methods. The results are shown in Table 1.
[Evaluation Methods]
Defoaming Property (Initial):

Mixtures of the respective defoamer samples added to a commercially sold aqueous cutting oil (Yushiroken FGE234, made by Yushiro Chemical Industry Co., Ltd.) in an amount of 0.2% by weight as their effective ingredients were each diluted with water to 1:30, followed by agitation in a 1 liter beaker under conditions of 8,000 rpm×10 minutes by means a homo mixer. At the time when the agitation was made for 10 minutes, the volume of the solution and the formed foams and a time of from the stop of the agitation till the foams completely disappeared were measured.
Defoaming Property (After 50° C.×7 Days):

Mixtures of the respective defoamer samples added to the above aqueous cutting oil in an amount of 0.2% by weight as their effective ingredients were stored at 50° C. for 7 days and each diluted with water to 1:30, followed by agitation in a 1 liter beaker under conditions of 8,000 rpm×10 minutes by means a homo mixer. At the time when the agitation was made for 10 minutes, the volume of the solution and the formed foams and a time of from the stop of the agitation till the foams completely disappeared were measured.
Internal Addition Stability:

Mixtures of the respective defoamer samples added to the above aqueous cutting oil in an amount of 0.2% by weight as their effective ingredients were stored at 50° C. for 7 days, after which their appearances were visually observed based on the following standards.

◯: No suspended and precipitated matter observed
Δ: Suspended and precipitated matter slightly observed
x: Suspended and precipitated matter appreciably observed

TABLE 1

| | Deforming Properties | | | | |
|---|---|---|---|---|---|
| | Initial | | After 50° C. × 7 days | | |
| | Volume (ml) after agitation | Time before defoaming | Volume (ml) after agitation | Time before defoaming | Internal addition stability |
| Example 1 | 580 | 0'30" | 620 | 0'50" | ◯ |
| Example 2 | 560 | 0'20" | 600 | 0'40" | ◯ |
| Example 3 | 650 | 0'45" | 720 | 1'10" | ◯ |
| Example 4 | 760 | 1'45" | 800 | 2'00" | ◯ |
| Example 5 | 750 | 1'20" | 780 | 2'10" | ◯ |
| Comparative Example 1 | 800 | 2'10" | 950 | 8'30" | Δ |
| Comparative Example 2 | 780 | 1'50" | >1,000 | >10 minutes | Δ |
| Comparative Example 3 | 950 | 6'30" | >1,000 | >10 minutes | X |

◯: No suspended and precipitated matter observed
Δ: Suspended and precipitated matter slightly observed
X: Suspended and precipitated matter appreciably observed Japanese Patent Application No. 2011-085087 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An oil compound used for defoaming comprising:
   (A) 100 parts by weight of a substantially hydrophobic organopolysiloxane having a viscosity of 10 to 100,000 mm$^2$/second at 25° C.; and
   (B) 1 to 20 parts by weight of finely divided silica that has undergone surface hydrophobization treatment,
   wherein when an insoluble matter is collected from the oil compound by using hexane and the spectra of the insoluble matter are measured by $^{29}$Si-CP/MAS-NMR, the peaks due to SiO$_{4/2}$ (Q) units on the silica surface are such that a ratio [(Q2+Q3)/Q4] between the total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group, is at 70/30 to 20/80.

2. The oil compound as defined in claim 1, wherein in the spectra measured by the $^{29}$Si-CP/MAS-NMR, a ratio (M/D) between the peak areas of triorganosiloxy units (M) and diorganosiloxy units (D) on the finely divided silica surface is at 80/20 to 10/90.

3. The oil compound as defined in claim 1, wherein the oil compound is obtained by mixing the ingredient (A) and the ingredient (B) in the presence of an alkaline catalyst.

4. A defoamer composition comprising the oil compound defined in claim 1.

5. The defoamer composition as defined in claim 4, wherein the composition is made of a solution dispersing the oil compound in a solvent.

6. The defoamer composition as defined in claim 4, wherein the composition is of a self-emulsifying type wherein the oil compound is used in combination with an organopolysiloxane modified with a polyoxyalkylene group.

7. The defoamer composition as defined in claim 4, wherein the composition is of an emulsion type wherein the oil compound is emulsified.

8. A method for evaluating a deforming performance, characterized in that when an oil compound containing finely divided silica having undergone hydrophobization treatment on the surface thereof is subjected to collection of an insoluble matter therefrom by using hexane and the spectra of the insoluble matter are measured by $^{29}$Si-CP/MAS-NMR, the oil compound whose spectral peaks due to the SiO$_{4/2}$ (Q) units on the surface of the finely divided silica in the resulting spectra are such that a ratio [(Q2+Q3)/Q4] between a total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group is at 70/30 to 20/80, is evaluated as showing a good defoaming performance.

9. A method for evaluating a deforming performance, characterized in that when an oil compound containing finely divided silica having undergone hydrophobization treatment on the surface thereof is subjected to collection of an insoluble matter therefrom by using hexane and the spectra of the insoluble matter are measured by $^{29}$Si-CP/MAS-NMR, the oil compound whose spectral peaks due to the SiO$_{4/2}$ (Q) units on the surface of the finely divided silica are such that a ratio [(Q2+Q3)/Q4] between a total area (Q2+Q3) wherein Q2 is a peak area of a silicon atom having two unreacted silanol groups and Q3 is a peak area of a silicon atom having one unreacted silanol group and an area Q4 wherein Q4 is a peak area of a silicon atom having no unreacted silanol group is at 70/30 to 20/80 and which has a ratio (M/D) between the peak area of triorganosiloxy units (M) and the peak area of diorganosiloxy units (D) on the finely divided silica surface being at 80/20 to 10/90, is evaluated as showing a good defoaming performance.

* * * * *